United States Patent [19]

Masuya et al.

[11] 3,966,778

[45] June 29, 1976

[54] PRODUCTION OF 21-PHOSPHATE CORTICORDS HAVING UNPROTECTED HYDROXYL RADICALS AT LEAST AT THE 17α- AND 21-POSITION

[75] Inventors: Hirotomo Masuya, Kobe; Takuichi Miki, Amagasaki, both of Japan

[73] Assignee: Takeda Chemical Industries, Ltd., Osaka, Japan

[22] Filed: June 20, 1974

[21] Appl. No.: 481,906

Related U.S. Application Data

[63] Continuation of Ser. No. 160,205, July 6, 1971, abandoned, which is a continuation of Ser. No. 547,779, May 5, 1966, abandoned.

[30] Foreign Application Priority Data

May 8, 1965 Japan.............................. 40-27042
June 9, 1965 Japan.............................. 40-34556

[52] U.S. Cl................... 260/397.45; 260/239.55 D
[51] Int. Cl.²............................................. C07J 5/00
[58] Field of Search............................ 260/397.45; /Machine Searched Steroids

[56] References Cited

UNITED STATES PATENTS

| 2,950,298 | 8/1960 | Elks et al. ...................... 260/397.45 |
| 3,053,834 | 9/1962 | Fried.............................. 260/239.55 |
| 3,073,816 | 1/1963 | Irmscher et al................. 260/239.5 |
| 3,487,077 | 12/1969 | Wendler et al. .............. 260/239.55 |
| 3,764,616 | 10/1973 | Elks et al. ...................... 260/397.45 |

*Primary Examiner*—Ethel G. Love
*Attorney, Agent, or Firm*—Wenderoth, Lind & Ponack

[57] ABSTRACT

There is disclosed a process for preparing 17α-hydroxy corticoid 21-phosphate which comprises reacting a compound selected from the group consisting of 17α,21-dihydroxy corticoid and 11, 17α,21-trihydroxy corticoid with pyrophosphoryl tetrachloride, subjecting the reaction mixture to a hydrolyzing agent and recovering the objective 17α-hydroxy corticoid 21-phosphate or 11, 17α-dihydroxy corticoid 21-phosphate from the hydrolysis reaction medium.

19 Claims, No Drawings

PRODUCTION OF 21-PHOSPHATE CORTICORDS HAVING UNPROTECTED HYDROXYL RADICALS AT LEAST AT THE 17<- AND 21-POSITION

This is a continuation of application Ser. No. 160,205, filed July 6, 1971 now abandoned, which application is in turn a continuation of application Ser. No. 547,779, filed May 5, 1966 (now abandoned).

This invention relates to a novel process for preparing 21-phosphates of corticoid-type steroids, said phosphates being characterized by their good solubility in water and by their prompt therapeutic effect (cortisone-like anti-inflammatory activity).

One of the most advantageous methods hitherto known of producing these 21-phosphates of corticoid-type steroids is that of British Pat. Nos. 913941 and 914943, which comprises the steps of (1) reacting the appropriate 21-hydroxy compound with methane sulfonyl halide to form the corresponding 21-methane sulfonate, (2) reacting the 21-methane sulfonate with alkali metal iodide thereby forming the corresponding 21-iodo compound, (3) reacting the 21-iodo compound with a mixture of silver phosphate and phosphoric acid to give the desired 21-phosphate of corticoid-type steroid, and (4) recovering the latter from the reaction mixture. However, this prior process requires four complicated steps as outlined above in order to obtain the objective compound from the corresponding 21-hydroxy compound. Further, the reagents employed are expensive and the yield is very low (about 35%).

Moreover, it is unavoidable that the crude 21-phosphate of corticoid-type steroid prepared by the process is contaminated with inorganic ions such as alkali metal ion, chloride ion, iodide ion, phosphate ion, etc. or organic amine, and it is extremely difficult to remove these impurities, especially inorganic phosphoric acid ion. To avoid these difficulties, a purifying method is proposed in U.S. Pat. No. 2,932,657 and also in British Pat. No. 886,869, which method comprises (1) contacting the crude 21-phosphate solution with a silver salt or an anion ion-exchange resin having an anion exchangeable with the inorganic phosphate ions of the solution to remove the inorganic phospate, (2) treating the solution obtained by step (1) with a zinc salt or suitable amine salt to precipitate the corresponding zinc or amine salt of the steroid phosphate, (3) acidifying the zinc or amine steroid phosphate with a cation ion-exchange resin and (4) recovering the pure 21-phosphate. However, this purification process is very complex and requires ion exchange resin and solvent in a rather large quantity to remove the inorganic phosphate completely, thus requiring a relatively long time and a complicated purification process. Therefore, neither the hitherto-known synthetic process nor the purifying process can be industrially profitable.

According to the present invention, 21-hydroxy corticoid is easily esterified by reaction with pyrophosphoryl tetrachloride, followed by hydrolysis, to obtain the corticoid 21-phosphate in much better yield (at least about 70%) than in the above-mentioned known method described in British Pat. Nos. 913941 and 914943. This is wholly surprising, unforeseeable and unexpected, particularly as the esterification of the 21-hydroxy corticoid-type steroid cannot be accomplished at all by using any other conventional phosphorylating agent such as phosphorus oxychloride, phosphorus pentachloride, polyphosphoric acid, etc. which have been commonly used for the phosphorylation of alcohols; that is to say, it seems that these agents do not react with 21-hydroxy corticoid-type steroid or, even if they react, they do not yield esters but 21-chlorinated compounds. On the other hand, it is also known that 11-hydroxy corticoid-type steroids such as hydrocortisone acetate, prednisolone, etc., are easily dehydrated in the presence of phosphorus oxychloride to give a compound having a double bond at the 9(11)-position (S. Bernstein et al; J.A.C.S., Vol. 75 (1953), Page 4830) and it is needless to say that such dehydrating reaction would be an undesirable side-reaction for the present process.

However, unexpectedly, according to this invention, the reaction of 21-hydroxy corticoid with pyrophosphoryl tetrachloride is not accompanied at all by such dehydrating reaction. It is, therefore, wholly surprising and not to be expected by the art-skilled, that 21-phosphate of corticoid-type steroid can be easily obtained in good yield without any appreciable side-reaction by the reaction of 21-hydroxy corticoid-type steroid with pyrophosphoryl tetrachloride.

Furthermore, and again unexpectedly, according to this invention, when crude 21-phosphate of corticoid-type steroid contaminated with inorganic phosphate, etc. is treated with activated charcoal, only the 21-phosphate is adsorbed, and the thus-absorbed 21-phosphate is, after washing with water, easily extracted with a neutral or alkaline solvent to give the pure corticoid 21-phosphate.

It is an object of the present invention to provide a novel and industrially profitable process for preparing corticoid 21-phosphates.

Another object of the present invention is to provide a novel and simple process for purifying a crude 21-phosphate solution contaminated with inorganic phosphate, etc.

Other objects will become apparent from the detailed description hereinafter provided.

The present method comprises reacting 21-hydroxy corticoid with pyrophosphoryl tetrachloride, followed by subjecting the reaction product to hydrolysis.

According to the present invention, the 21-hydroxy corticoid is first reacted with pyrophosphoryl tetrachloride. The pyrophosphoryl tetrachloride can be synthesized, for example, by so-called Grunze's method (H. Grunze; Chemische Berichte, Vol. 92 (1959), Page 850). The corticoid-type steroids (corticoids) employed as starting material are exemplified by compounds having the so-called corticoid-type steroid skeleton, for example, hydrocortisone, cortisone, prednisolone, prednisone, dexamethasone, betamethasone, 9α-fluoro-16-methylene-prednisolone, corticosterone, and so on, whereby there are obtained the corresponding hydrocortisone-21-phosphate, cortisone-21-phosphate, prednisolone-21-phosphate, prednisone-21-phosphate, dexamethasone-21-phosphate, betamethasone-21-phosphate, 9α-fluoro-16-methylene-prednisolone-21-phosphate, corticosterone-21-phosphate, etc., respectively, as such or as the (equivalent) alkali metal salt of the phosphate. The reaction proceeds smoothly in a solvent which does not react with the starting materials. As the solvent, there may be employed, for example, tetrahydrofuran, dioxane, pyridine, acetonitrile, hydrocarbons (e.g. benzene, toluene, xylene), phenols (e.g. phenol, cresol), etc. The reaction is generally carried out at room temperature (20° to 30°C) or under cooling, to complete the reaction within several hours.

Preferably the reaction temperature is below about −10°C and may be as low as −50°C.

Then, the obtained reaction mixture is subjected to hydrolysis to produce the corticoid 21-phosphate. The hydrolysis is carried out in aqueous medium, and is accelerated by the presence of basic material such as sodium hydroxide, potassium hydroxide, lithium hydroxide, pyridine, picoline, etc. The hydrolysis reaction is generally carried out at room temperature or under cooling.

The solution containing the corticoid 21-phosphate thus obtained is often contaminated with inorganic phosphate and other impurities. If desired, therefore, the solution may be subjected to purification. While any conventional purification process may be employed, that with activated charcoal is most preferable. That is, the reaction solution is acidified by the addition of an acidic material such as hydrochloric acid, etc., and then treated with activated charcoal to adsorb the 21-phosphate of corticoid-type steroid. The activated charcoal is usually used in about 1 to 10 times by weight of 21-phosphate of corticoid-type steroid formed in the reaction solution.

The activated charcoal on which the corticoid 21-phosphate is absorbed is washed with water or an aqueous solution of methanol, ethanol, acetone, etc. to remove inorganic acid and is then extracted with a neutral or alkaline solvent. As the solvent, there can be used methanol or a solution of water, methanol or ethanol containing alkali metal hydroxide, such as lithium hydroxide, sodium hydroxide, potassium hydroxide, ammonia or organic amine. The extraction may be carried out at room temperature or under cooling in general, but may also be carried out under elevated temperature.

Thus-obtained extract solution is so pure that the solution may be used, after adjusting its pH value if desired, for pharmaceutical preparations. When there is used, as extracting solvent, the alkaline solution of pH 8–9 containing such an alkali metal hydroxide as sodium hydroxide, the extract may be directly used for pharmaceutical preparations. The free corticoid 21-phosphate is obtained by dealkalization of the extract solution or by using a neutral solvent for extraction. The corticoid 21-phosphate can be obtained in powder form by evaporation of the solvent under reduced pressure.

The free phosphate is readily convertible back to the alkali metal salt thereof and vice-versa, and these two forms are herein regarded as equivalent, as in fact they are.

The following examples are solely for the purpose of illustration and are not intended to be construed as limitations of this invention; minor variations may be resorted to without departing from the spirit and scope of this invention. In the examples, "g" and "ml" are "gram" and "milliliter", respectively. Temperatures are all uncorrected, and percentages are all on the weight basis.

EXAMPLE 1

While stirring a solution of 2 g of pyrophosphoryl tetrachloride in 20 ml of tetrahydrofuran at −50°C, a solution of 2 g of prednisolone in 40 ml of tetrahydrofuran is added thereto for 15 minutes to allow a reaction to take place. Temperature of the reaction mixture is elevated to −10°C in about 2.5 hours, whereupon the reaction is completed. The reaction solution is combined with 100 ml of ice-water to effect hydrolysis. After the pH is adjusted to about 7, tetrahydrofuran is removed by evaporation under reduced pressure, then the pH is again adjusted to pH 4.8–4.9. The resulting solution is treated with weakly basic anion-exchange resin (e.g. Amberlite IR-45), to remove the inorganic acid. Thus-obtained solution is freeze-dried to give colorless powder, which is washed with acetone, followed by extracting with methanol. The methanol extract is concentrated to give 2.0 g of sodium salt of prednisolone-21-phosphate.

EXAMPLE 2

To a solution of 0.63 g of pyrophosphoryl tetrachloride in 10 ml of tetrahydrofuran, a solution of 0.9 g of prednisolone in a mixture of 0.4 g of pyridine and 20 ml of tetrahydrofuran is added dropwise under stirring at −50°C. After standing under the same conditions, the reaction mixture is poured into an aqueous solution of sodium hydrogencarbonate and the resultant solution is subjected to distillation of the tetrahydrofuran under reduced pressure to give precipitates. The precipitates are collected by filtration and then dissolved in methanol, followed by filtering off insoluble inorganic matter. Methanol is evaporated off from the resultant solution to give 0.4 g of sodium salt of diprednisolone-21-phosphate. Melting point: 235°C.

The mother-liquor of the precipitates is freeze-dried to give powder, which is purified with a mixture of methanol-acetone to obtain 0.4 g of sodium salt of prednisolone-21-phosphate.

EXAMPLE 3

To a solution of 7.8 g of dexamethasone in 100 ml of tetrahydrofuran, a solution of 10 g of pyrophosphoryl tetrachloride in 20 ml of tetrahydrofuran is dropped under stirring at −40°C. After the temperature of the reaction mixture is kept at −40°C for 2 hours, 100 ml of water is added to the resulting solution, and then 20 g of activated charcoal is further added, followed by evaporating off tetrahydrofuran under reduced pressure. The activated charcoal onto which the steroid compounds are adsorbed is collected by filtration and washed with 500 ml of water to remove the inorganic acid. So-washed activated charcoal is added to 100 ml of methanol and the pH of the mixture is adjusted to 8.0 by gradually adding 15 ml of 2-normal methanolic sodium hydroxide. This mixture is filtered and the charcoal is washed with methanol several times. The combined methanolic solution is concentrated under reduced pressure to give 6.5 g of sodium salt of dexamethasone-21-phosphate which is recrystallized from a mixture of methanol and acetone to obtain colorless powder.

EXAMPLE 4

To a solution of 72 g of prednisolone in a mixture solvent of 660 ml of meta-cresol (of phenol) and 330 ml of tetrahydrofuran, 100 g of pyrophosphoryl tetrachloride is added dropwise under stirring at −35° to −40°C within 15 minutes. After keeping the reaction mixture at the same temperature for 50 minutes, 500 ml of water is added thereto to hydrolyze the excess phosphoryl tetrachloride. Ether is further added to the resultant solution and the organic phase is subjected to extraction with water and then with an aqueous solution of sodium hydrogencarbonate. The extracts are combined and then the pH adjusted to lower than 2.

200 g of activated charcoal is added to the combined extracts, followed by stirring the mixture to effect absorption of the steroid compounds on the charcoal. The charcoal is washed with water until the pH value of the washing solution is 4 and then the charcoal is put into 800 ml of methanol.

The mixture is neutralized by adding 180 ml of 2-normal methanolic solution of sodium hydroxide under stirring, and then subjected to filtration. Thus collected activated charcoal is washed with methanol several times. The combined methanolic solution is concentrated and acetone is added to the residue to precipitate sodium salt of prednisolone-21-phosphate, which is again subjected to a precipitation process employing methanol-acetone to give 85 g of the pure objective compound.

EXAMPLE 5

To 50 ml of an aqueous solution containing 5 g of prednisolone-21-phosphate, 4 g of phosphoric acid and 2 g of hydrogen chloride is added 15 g of activated charcoal, and the mixture is stirred. The activated charcoal is collected by filtration and washed with 100 ml of water. From the so-washed activated charcoal, the steroid compound is detached completely by the use of 50 ml of 10% aqueous ammonia and then 50 ml of water. The respective steroid solutions are combined, and 50 g of strongly acid sulfonated polystyrene ion exchange resin (e.g. Amberlite IR-120) is added thereto under ice-cooling and stirring to give an acid pH solution. To the solution is added an aqueous solution of sodium hydroxide to adjust the pH to 7.3, followed by removal of water under reduced pressure to give 5 g of powdery sodium salt of prednisolone-21-phosphate.

EXAMPLE 6

To a solution of 2 g of pyrophosphoryl tetrachloride in 20 ml of tetrahydrofuran, a solution of 2 g of hydrocortisone in 40 ml of tetrahydrofuran is added dropwise under stirring at −40°C for 15 minutes. The reaction solution is treated in a similar manner as in Example 1 to give 2.0 g of sodium salt of hydrocortisone-21-phosphate.

The alkali metal salt can, in each of the preceding Examples, be converted into the free phosphate, if desired, by per se conventional (dealkalization) methods.

What is claimed is:

1. A process for preparing 17α-hydroxy corticoid 21-phosphate which comprises reacting a compound selected from the group consisting of 17α,21-dihydroxy corticoid and 11,17α,21-trihydroxy corticoid with pyrophosphoryl tetrachloride in the presence of an organic solvent which does not react with the starting materials at a temperature of up to about room temperature, subjecting the reaction mixture to hydrolysis with an aqueous hydrolysis medium at a temperature up to about room temperature, and recovering the objective 17α-hydroxy corticoid 21-phosphate or 11,17α-dihydroxy corticoid 21-phosphate from the hydrolysis reaction medium.

2. A process according to claim 1, wherein the reaction with the pyrophosphoryl tetrachloride is carried out at ambient temperature.

3. A process according to claim 1, wherein the reaction with the pyrophosphoryl tetrachloride is carried out at a temperature below about −10°C.

4. A process according to claim 1, wherein the starting corticoid is prednisolone and the product is prednisolone-21-phosphate as such or as alkali metal salt.

5. A process according to claim 1, wherein the starting corticoid is dexamethasone and the product is dexamethasone-21-phosphate as such or as alkali metal salt.

6. A process according to claim 1, wherein the starting corticoid is hydrocortisone and the product is hydrocortisone-21-phosphate as such or as alkali metal salt.

7. A process according to claim 1, wherein the starting corticoid is cortisone and the product is coritsone-21-phosphate as such or as alkali metal salt.

8. A process according to claim 1, wherein the starting corticoid is prednisone and the product is prednisone-21-phosphate as such or as alkali metal salt.

9. A process according to claim 1, wherein the starting corticoid is betamethasone and the product is betamethasone-21-phosphate as such or as alkali metal salt.

10. A process according to claim 1, wherein the starting corticoid is 9α-fluoro-16-methylene-prednisolone and the product is 9α-fluoro-16-methylene-prednisolone-21-phosphate as such or as alkali metal salt.

11. A process according to claim 1, wherein the starting corticoid is corticosterone and the product is corticosterone-21-phosphate as such or as alkali metal salt.

12. A process according to claim 1, wherein pyrophosphoryl tetrachloride is employed in the amount of one to two moles against one mole of the corticoid.

13. A process according to claim 1 wherein the organic solvent is a member selected from the group consisting of tetrahydrofuran, phenols, and mixtures thereof.

14. A process according to claim 1 wherein the solvent is a mixture of tetrahydrofuran and cresol.

15. A process according to claim 1, wherein the solvent is a mixture of tetrahydrofuran and phenol.

16. A process according to claim 1, wherein the solvent is tetrahydrofuran.

17. A process according to claim 1, wherein the solvent is a phenol.

18. A process according to claim 17, wherein the solvent is phenol.

19. A process according to claim 17, wherein the solvent is cresol.

* * * * *